US009877751B2

(12) United States Patent
Tsuang et al.

(10) Patent No.: US 9,877,751 B2
(45) Date of Patent: Jan. 30, 2018

(54) BONE SCREW OF MINIMALLY INVASIVE FIXATION DEVICE FOR LUMBAR

(71) Applicant: BAUI Biotech Co., Ltd., New Taipei (TW)

(72) Inventors: Fon Yih Tsuang, New Taipei (TW); Chia Hsien Chen, New Taipei (TW); Chang Jung Chiang, New Taipei (TW); Yi Jie Kuo, New Taipei (TW)

(73) Assignee: BAUI BIOTECH CO., LTD., New Taipei (TW)

( * ) Notice: Subject to any disclaimer, the term of this patent is extended or adjusted under 35 U.S.C. 154(b) by 0 days.

(21) Appl. No.: 14/532,410

(22) Filed: Nov. 4, 2014

(65) Prior Publication Data

US 2015/0127054 A1    May 7, 2015

(30) Foreign Application Priority Data

Nov. 4, 2013    (TW) .............................. 102220508 U

(51) Int. Cl.
*A61B 17/70* (2006.01)
*A61B 90/00* (2016.01)

(52) U.S. Cl.
CPC ........ *A61B 17/7089* (2013.01); *A61B 17/708* (2013.01); *A61B 17/7032* (2013.01); *A61B 17/7037* (2013.01); *A61B 17/7079* (2013.01); *A61B 17/7085* (2013.01); *A61B 2090/037* (2016.02)

(58) Field of Classification Search
CPC .............. A61B 17/708; A61B 17/7083; A61B 17/7085; A61B 2019/307
See application file for complete search history.

(56) References Cited

U.S. PATENT DOCUMENTS

| | | | |
|---|---|---|---|
| 9,198,692 B1* | 12/2015 | Doose ................ | A61B 17/7032 |
| 2008/0119849 A1* | 5/2008 | Beardsley et al. .............. | 606/61 |
| 2010/0174325 A1* | 7/2010 | Won et al. ..................... | 606/305 |
| 2011/0166606 A1* | 7/2011 | Stihl .................. | A61B 17/7091 |
| | | | 606/279 |
| 2011/0202095 A1* | 8/2011 | Semler et al. ................ | 606/308 |
| 2012/0323278 A1 | 12/2012 | Tsuang et al. | |
| 2013/0172937 A1* | 7/2013 | Davenport ......... | A61B 17/7032 |
| | | | 606/278 |
| 2016/0008034 A1* | 1/2016 | Stokes ............... | A61B 17/7085 |
| | | | 606/278 |

* cited by examiner

*Primary Examiner* — Jan Christopher Merene
*Assistant Examiner* — Atiya Mahmud
(74) *Attorney, Agent, or Firm* — Juan Carlos A. Marquez; Marquez IP Law Office, PLLC

(57) ABSTRACT

A bone screw of minimally invasive fixation device for lumbar comprises a positioning casing and a screw body. The positioning casing includes a rod securing base and an alignment portion, both of which are integrally formed; an annular notch is formed between them. The alignment portion has at least two pairs of rod alignment openings in a bulb-shaped or keyhole-shaped form with an upper portion larger than a lower portion. Two longitudinal notches extend from near the top across the alignment openings to the rod securing base. The screw body includes a spherical head and a screw rod; the outer diameter of the spherical head is larger than that of the screw rod. The screw body is rotatably connected to the bottom portion of the positioning casing; the spherical head of the screw body is arranged in the spherical pit of the rod securing base.

11 Claims, 8 Drawing Sheets

BONE SCREW OF MINIMALLY INVASIVE FIXATION DEVICE FOR LUMBAR

BACKGROUND OF THE INVENTION

1. Field of the Invention

The invention relates to a bone screw, especially to a bone screw of minimally invasive fixation device for lumbar.

2. Description of the Related Art

Any displacement of or compression on the spine or even the tension of surrounding muscles or ligaments can directly influence the nerves in the spine and indirectly lead to difficulty with moving, causing aches, or discomfort caused by the organs located at the distal ends which the nerves reach, the muscles, or glands. Generally, a surgery to install a fixation device between the vertebras can be applied to treat such symptoms for releasing the pressure. In some cases, an intervertebral discectomy is performed to remove the malfunctioning intervertebral discs between the vertebras and an interbody fusion cage is arranged at the removing position for reconstructing the height of adjacent vertebras, and fixation device is installed between the vertebras. As a result, the vertebras can be secured and aligned in the following healing procedures.

In the conventional surgery of installing a fixation device, bone screws are first implanted into and secured to the upper and lower two vertebras or the appropriate positions of multiple vertebras to be secured. The bone screws have rod securing bases at each top end for securing a rod between the bone screws to connect and configure the bone screws into a rigid securing rod structure so that the positioning between the vertebras is maintained and an appropriate supporting force is provided to achieve the function of releasing pressure and maintaining alignment.

Up to now, minimally invasive surgeries of spinal fixation device have been applied in treating pathological changes of vertebras since such surgeries result in small wounds, largely reduce damage to the treating portions and the neighboring tissues for improving the safety of operation, and decrease the time period of healing and recovery.

A conventional technique such as US publication No. US 2012/0323278 A1, entitled "MINIMALLY INVASIVE SPINAL STABILIZATION SYSTEM," discloses a minimally invasive spinal fixation device for providing relative fixation of a series of vertebras comprising a securing rod and a plurality of bone screws. Each bone screw includes an upper portion and a thread body. The upper portion is configured to receive a portion of the securing rod. The thread body extends from a first end of the upper portion and is configured to engage one of the vertebras. The device further comprises an engaging member which includes a plurality of outer threads configured to engage a plurality of threads correspondingly formed on an inner surface of the upper portion. The securing rod is secured to the upper portion by the engaging member. The upper portion comprises a separation area which is weaker than the other portions of the upper portion so that a position is defined for easily separating the first portion of the upper portion from the other portions of the upper portion at the position when a sufficient force is applied to at least the first portion of the upper portion.

The specific structure of the bone screw is illustrated in FIG. 4. A bone screw has an upper portion 30 and a thread body 40. The upper portion 30 of the bone screw is in the form of a tube having a U-shaped hollow portion 35. An annular notch 36 in the upper portion divides the upper portion 30 into two portions: a securing base 31 and a separation area 32. While operating the minimally invasive surgery of the spinal fixation device, the thread bodies 40 of multiple bone screws are respectively screwed into multiple vertebras, but the opening at the top end of the upper portion 30 remains above the skin. A ruler-like alignment fixture is applied to align the upper portion 30 of each bone screw for aligning the height of the implanted bone screws and making the longitudinal axes of the U-shaped hollow portions 35 of the bone screw upper portions 30 parallel with each other so that a securing rod can be arranged on the securing bases 31 of the bone screw upper portions. Then, the opening at the top of the upper portion 30 is covered with a cap 60 for supporting and stabilizing the separation area 32 which is a relatively weaker structure at the upper two sides of the upper portion 30. As a result, the successive installation of the securing rod and removing of the separation area 32 at the two sides of the upper portions 30 go well and smoothly.

The upper portion 30 of the bone screw is split at its upper portion to form the separation area 32, so the structure of the separation area 32 is relatively weak. While encountering an external force under operation of implanting bone screws or fixing the securing rod, the bone screw could break or deform to impede the surgery and even adversely influence the result of the surgery. Even though a cap 60 is installed at the top opening of the upper portion to address the aforementioned shortcoming, such complicated structure not only increases the complexity of assembling these components during surgery but also increases the time period and risk of the surgery. Moreover, although the conventional structure of a bone screw allows a small portion of the upper portion 30 to remain above the skin for inserting a ruler-like alignment fixture after implantation of the bone screw, owing to the difference in angle of each vertebra, it is still not easy to accurately conform the height of the implanted bone screws to the curvature of the spine with the ruler-like alignment fixture. In addition, the ruler-like alignment fixture is to align the positions and angles of the upper portions 30 of multiple bone screws by receiving the small top portions of the upper portions in a guiding slot. However, the cross-section of the U-shaped hollow portion 35 of the upper portion 30 is perpendicular to the axis of the guiding slot of the alignment fixture, so it is difficult to make the longitudinal axes of the U-shaped hollow portion 35 of the upper portion 30 accurately parallel to each other through the alignment by the guiding slot. Failing to make the longitudinal axes of the U-shaped hollow portion 35 parallel to each other will lead to interference while installing the securing rod, and thus installing the securing rod on the securing bases 31 of the bone screw upper portions cannot be smoothly accomplished.

SUMMARY OF THE INVENTION

It is an object of this invention to provide a bone screw structure of minimally invasive fixation device for lumbar which is convenient for accurate positioning from outside human body and comprises an elongated positioning casing so that at least part of the alignment portion of the positioning casing will be exposed to the outside of human body for aligning the fixation positions and arranging angles by an alignment rod fixture after the implantation of each bone screw while performing minimally invasive surgery. The efficiency and accuracy of installing a fixation device during minimally invasive surgery can be improved.

It is another object of this invention to provide a bone screw structure of a minimally invasive fixation device for lumbar with a simplified structure. The positioning casing has a top opening which is enclosed by the side wall so as to prevent the positioning casing from being deformed or damaged during surgery, and thus an additional cap will not be necessary for strengthening the structure. As a result, the operating procedure can be simplified and the time period of performing surgery can be reduced. Moreover, the positioning casing is configured with longitudinal notches and annular notches for removing the positioning casing after breaking by applying an external force on the side wall.

In order to achieve the above objects, this invention provides a bone screw convenient for fixing and for accurate alignment, at least comprising a positioning casing and a screw body, the positioning casing being substantially cup-shaped and including a rod securing base and an alignment portion, the rod securing base and the alignment portion being integrally configured and defined by an annular notch therebetween; a bottom wall of the rod securing base having a spherical pit, a through hole being arranged on a bottom center portion of the spherical pit, an inner hole surface above the spherical pit being configured with a thread, and a side wall of the rod securing base being configured with a pair of U-shaped openings aligned perfectly such that a securing-base-passing passage is formed between the pair of U-shaped openings and laterally passing through the rod securing base; the wall of the alignment portion has at least one pair of openings aligned perfectly such that each of the pairs of openings is configured with an alignment-portion-passing passage laterally passing through the alignment portion, and the multiple pairs of openings including two pairs of rod alignment openings and a pair of ∩-shaped openings, wherein the pair of ∩-shaped openings are respectively connected with the U-shaped openings of the rod securing base, and wherein the side wall at adjacent positions of the openings is configured with longitudinal notches; and the screw body comprising a spherical head and a screw rod, the outer diameter of the spherical head being larger than an outer diameter of the screw rod, the spherical head being connected to a top portion of the screw rod, the spherical head being configured with a joint notch corresponding to the shape of a driving tool and a non-slip texture for increasing the frictional force on the outer surface of the spherical head, the screw rod being configured with an outer thread, and the front portion of the screw rod having a tip with an acute angle; wherein the screw body is rotatably connected to the bottom portion of the positioning casing such that the spherical head of the screw body is arranged in the spherical pit of the rod securing base; and the alignment portion of the positioning casing can be broken into two pieces and separated from the rod securing base by applying an force to the wall and breaking the longitudinal notches and the annular notch to remove the alignment portion from the positioning casing.

In particular, the positioning casing is substantially an elongated cup-shape hollow member with a length ranging from 85 mm to 110 mm. Thus, most areas of the alignment portion remain above the skin for operating alignment after implanting the bone screws into the vertebras.

Specifically, the shapes of the rod alignment openings are in a bulb-shaped or keyhole-shaped form with an upper portion larger than a lower portion. The opening shapes cause the assembly and adjustment of alignment fixtures to be carried out easily and fast for largely reducing the time period of surgery.

The functions and technical features of this invention are further specified in the following descriptions for persons of ordinary skills in the art to carry out the present invention in view of the present specification.

DETAILED DESCRIPTION OF THE INVENTION

Figure 1:
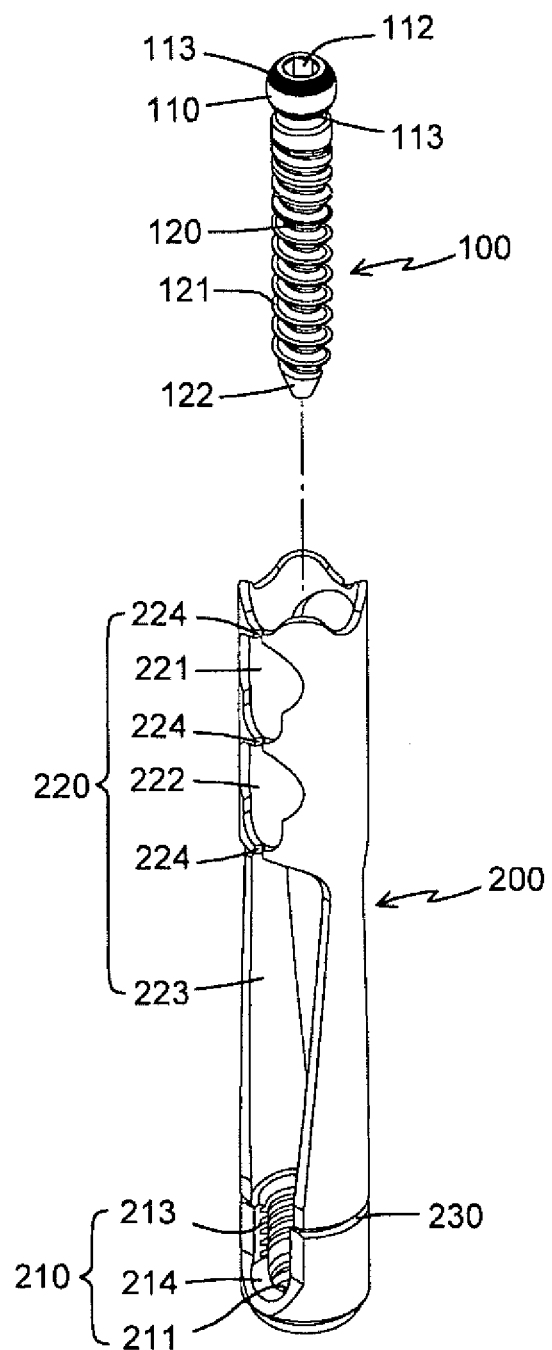
FIG. 1 illustrates a perspective view of the bone screw in a disassembled state according to an embodiment of the present invention.
Figure 2:
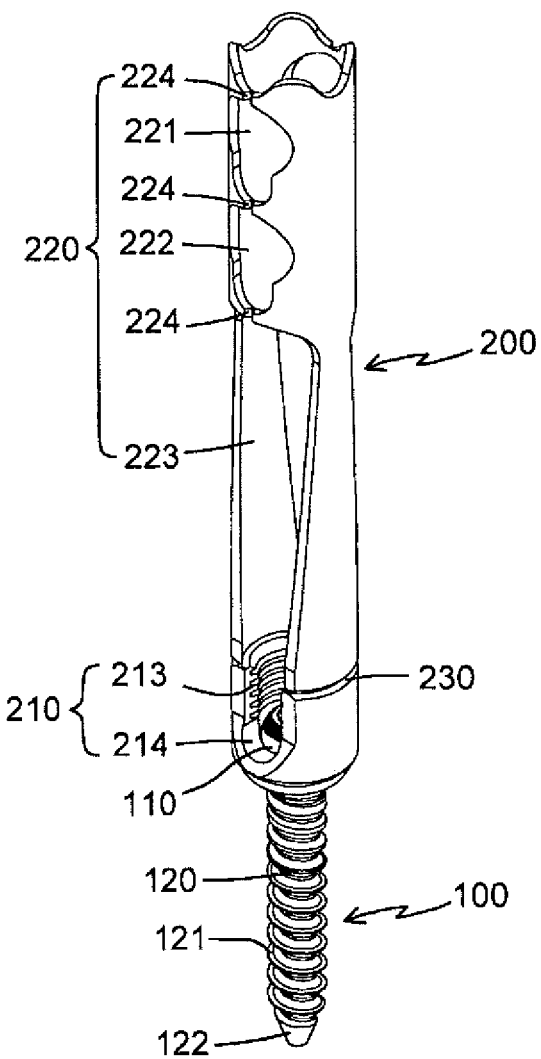
FIG. 2 illustrates a perspective view of the bone screw in an assembled state according to an embodiment of the present invention.

As shown in FIGS. 1 and 2, the bone screw of minimally invasive fixation device for lumbar according to an embodiment of the invention includes a positioning casing 200 and a screw body 100. The positioning casing 200 is substantially in a form of an elongated cup-shape and includes a rod securing base 210 and an alignment portion 220. An annular notch 230 on the positioning casing 200 is formed between the rod securing base 210 and alignment portion 220. The bottom of the rod securing base 210 includes a spherical pit 211 and a though hole configured at the bottom center portion of the spherical pit 211. The inner surface right above the spherical pit 211 is configured with a thread 213 and the wall of the rod securing base 210 is configured with a pair of U-shaped openings 214 that are perfectly aligned such that a securing-base-passing passage laterally passing through the rod securing base is defined by the U-shaped openings 214. The wall of the alignment portion 220 has at least one pair of alignment openings, preferably two pairs of rod alignment openings 221, 222 and a pair of ∩-shaped openings 223; two alignment-portion-passing passages laterally passing though the alignment portion 220 are defined by each of the pairs of the openings 221, 222. The pair of ∩-shaped openings 223 are adjacent to the U-shaped openings 214 of the rod securing base 210 and the pair of ∩-shaped openings 223 and the U-shaped openings 214 of the rod securing base 210 communicate with each other. Longitudinal notches 224 are formed on the wall of the alignment portion 220 and adjacent to the openings 221, 222. The annular notch 230 and the longitudinal notches 224 are weaker portions of the positioning casing 200 because the thicknesses of them are thinner that the other portion. Thus, applying a sufficient but not very large force to the two side walls of the alignment portion 220 adjacent to the notches 224 can easily separate the two side walls of the alignment portion from each other and separate the alignment portion 220 from the rod securing base 210.

The screw body 100 includes a spherical head 110 and a screw rod 120. The outer diameter of the spherical head is larger than that of the screw rod, and the spherical head is connected to the top end of the screw rod. The spherical head 110 is configured with a joint notch 112 which conforms to the shape of a driving tool so that the driving tool can at least partly insert and match with the joint notch 112 and drive the screw body 100. The joint notch 112 may be, for example, a notch of a hexagonal shape or other polygonal shapes, a cruciform shape or a slotted shape, etc. The outer surface of the spherical head is configured with a non-slip texture 113 to increase the frictional force for improving the stability after securing. The screw rod 120 is configured with an outer thread 121, and the front portion of the screw rod includes a screw tip 122 in the form of an acute angle to facilitate the screw rod 120 to be screwed into bones.

As shown in FIG. 2, the screw body 100 is rotatably connected to the bottom portion of the positioning casing 200 by passing the screw rod 120 through the through hole of the bottom wall of the rod securing base 210 and extending outwardly; the spherical head 110 of the screw body 100 is maintained in the spherical pit 211 of the rod securing base 210 because the outer diameter of the spherical head 110 is larger than that of the through hole of the bottom wall of the rod securing base 210.

Figure 3A:
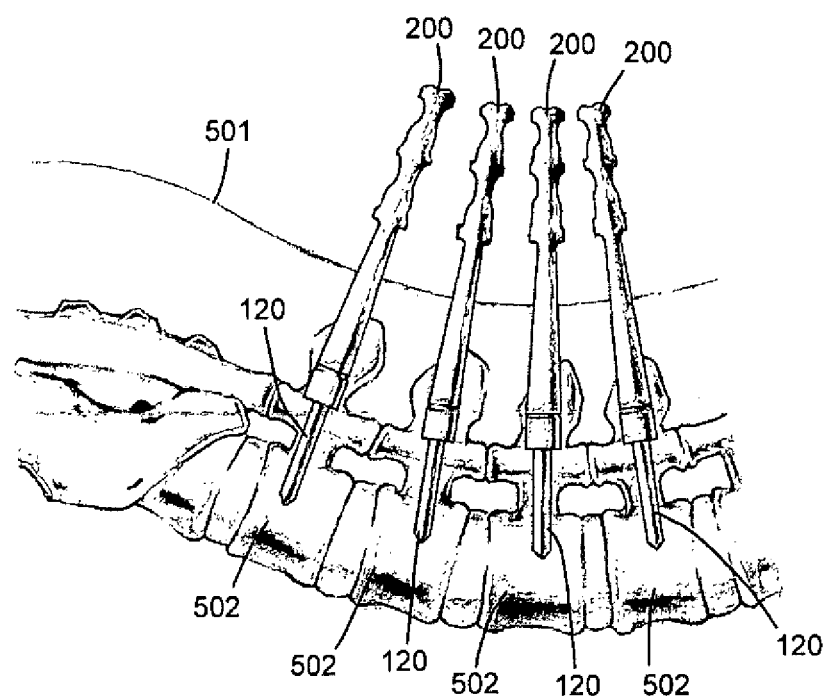
FIG. 3A illustrates a state during an operation; multiple bone screws are implanted into vertebras according to an embodiment of the present invention.

FIGS. 3A-3E present fixing a fixation device on the vertebras during minimally invasive surgery and illustrate the application method of the bone screw of the present invention. During minimally invasive surgery, the bone screw is inserted into the wounds of skin 501. Then, a driving tool is inserted through the hollow longitudinal space of the positioning casing 200 and into the joint notch 112 of the spherical head of the screw rod to drive the screw rod 120 so that the screw rod 120 is implanted into the vertebra 502. The vertebra is positioned under the skin with a depth of about 35 mm to 50 mm for a general person; the length of the positioning casing 200 is designed to be about 100 mm, so that a large portion of the alignment portion 220 of the positioning casing 200, in particular, the portions of the two pairs of the rod securing openings 221 and 222 on the side wall of the alignment portion, stay above the skin after the bone screw is implanted into the vertebra 502. The foregoing operation procedures are repeated to steadily implant several (generally two to four) bone screws into adjacent vertebras 502. The embodiment illustrated in FIG. 3A presents four bone screws respectively implanted into four vertebras.

Figure 3B:
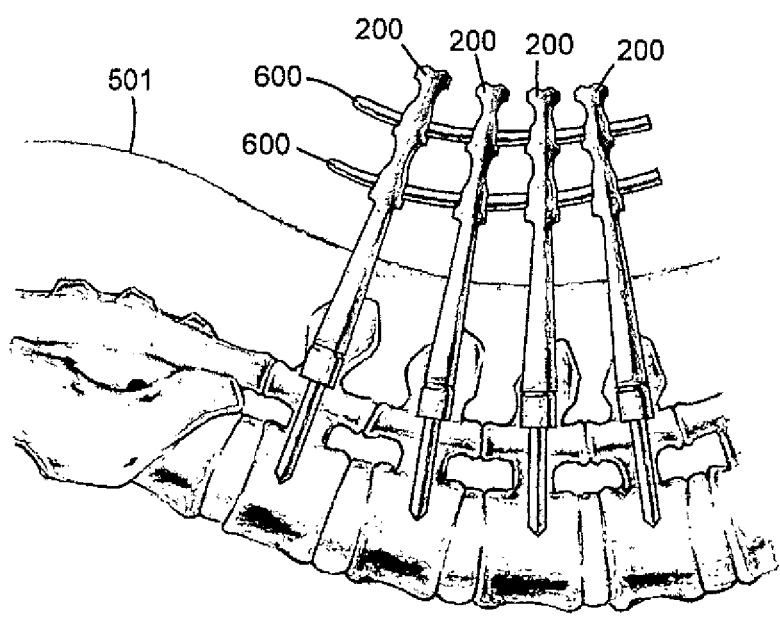
FIG. 3B illustrates a state during an operation; multiple bone screws are implanted into vertebras and aligned with a rod fixture according to an embodiment of the present invention.
Figure 3C:
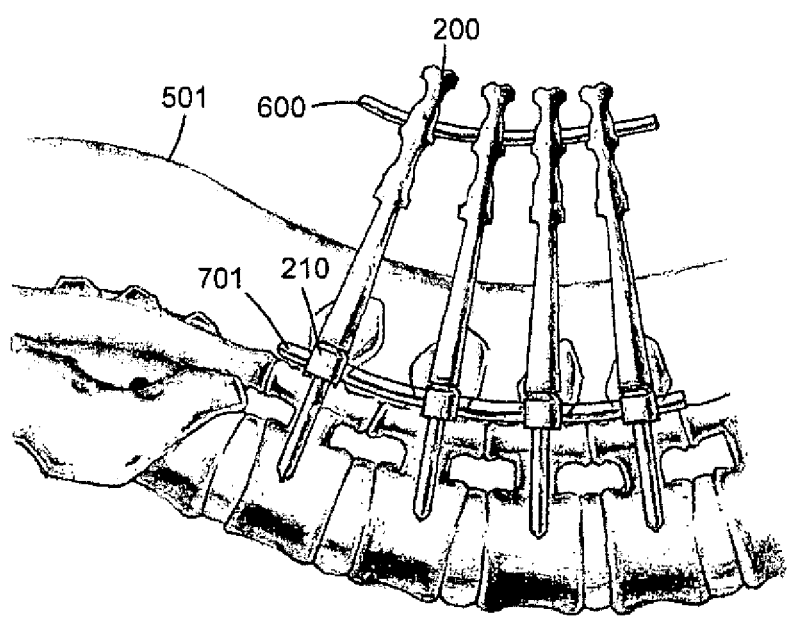
FIG. 3C illustrates a state during an operation; multiple bone screws are implanted into vertebras and temporarily secured with a rod fixture; a rod is placed on the rod securing base according to an embodiment of the present invention.
Figure 3D:
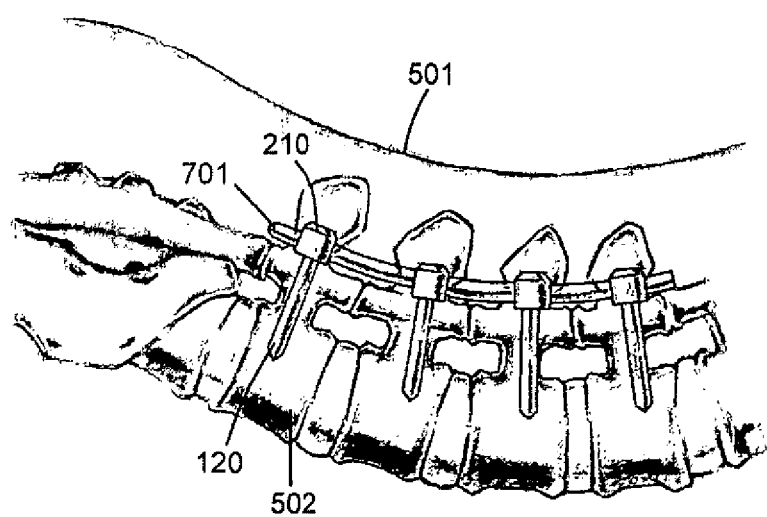
FIG. 3D illustrates a state during an operation; after the bone screws are implanted and the rod is secured to the rod securing bases, the alignment portion is removed from the positioning casing according to an embodiment of the present invention.
Figure 3E:
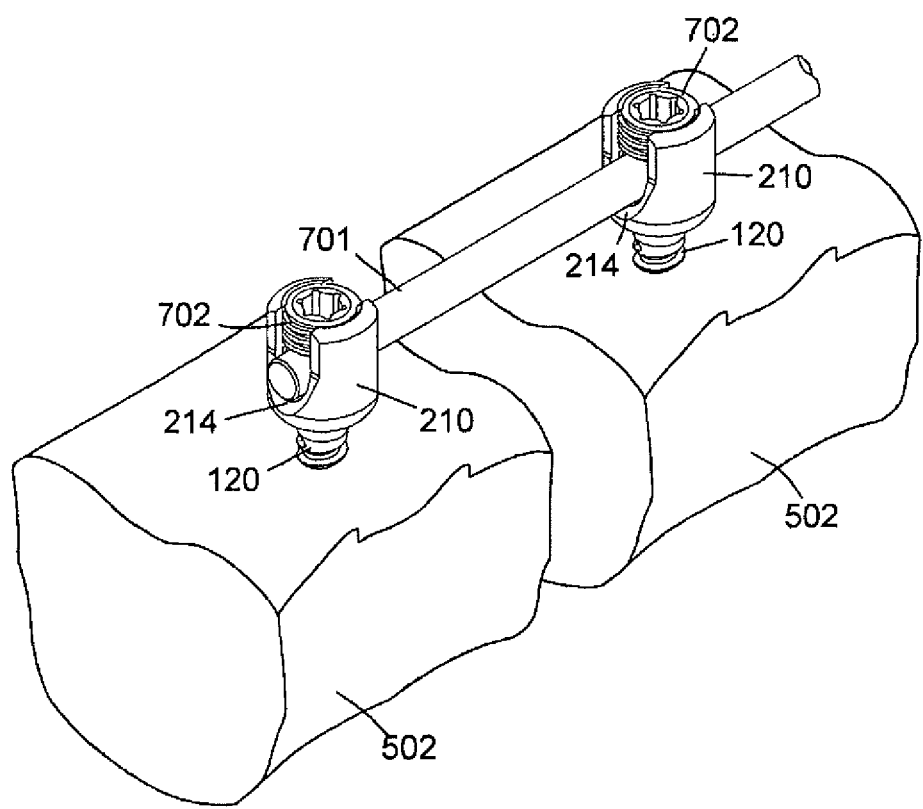
FIG. 3E illustrates a schematic perspective view of the appearance that the bone screw with the rod have been secured to the vertebras according to an embodiment of the present invention.
Figure 4:
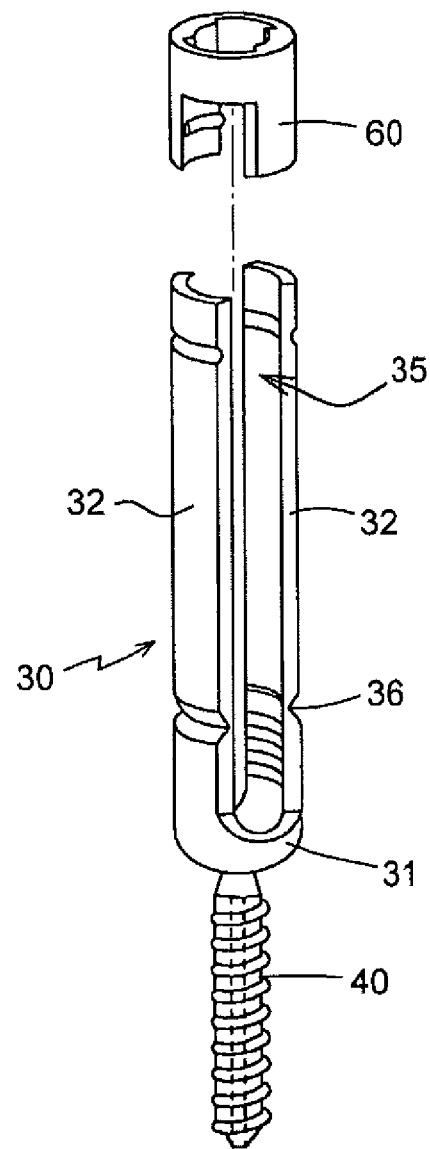
FIG. 4 illustrates a schematic perspective view of a conventional bone screw structure.

As shown in FIG. 3B, subsequently, an alignment fixture 600 is applied to align with the rod alignment openings 221 and 222 of the alignment portions 220 of each positioning casing 200. The alignment fixture 600 has a curvature the same as that of the spine to which the fixation device for vertebra is fixed. The fixation positions and angles of each bone screw are adjusted by inserting an alignment fixture 600 through a series of openings 221 and inserting another alignment fixture 600 through a series of openings 222. After alignment, the disposition of the rod securing openings 221 and 222 of the bone screws conforms to the curvature of the spine. The opening shapes of the rod alignment openings 221, 222 are in a bulb-shape or keyhole-shape with an upper portion larger than a lower portion so that the assembly and adjustment of the alignment fixture 600 are rendered easy and fast for largely reducing the time period of a surgery. In the embodiment, the alignment portion 220 includes two pairs of rod alignment openings 221, 222 so that the bone screws can be positioned on the same plane after alignment. Therefore, the operation of aligning the fixation positions and angles of the bone screws is easier and better accuracy can be achieved. The alignment fixture 600 has a structure corresponding to the rod 701 of the vertebra to be fixed. Thus, the rod 701 can be accurately arranged on the rod securing base 210 of each positioning casing 200.

After aligning the alignment fixture 600 with the bone screw, a rod 701 is disposed through the U-shaped opening 214 of each rod securing base 210 and a set screws (grub screw) 702 corresponding to the thread 213 of the inner hole is configured for securing the rod 701 to the rod securing base 210 of each bone screw positioning casing 200. Then, a separation tool (not presented in the drawings) is extended into the positioning easing 200 to apply an outwardly opening force to the side wall of the alignment portion 220 of the positioning casing such that the annular notch 230 and longitudinal notches 224 are broken. As a result, the alignment portion 220 is broken into two pieces and separated from the rod securing base 210 and the broken pieces of alignment portion 220 are removed from the body so that installation of the fixation device on the spine is accomplished.

Although the present invention has been described in relation to particular embodiments thereof, the present invention is not limited by such descriptions. All kinds of substitutions, changes, or transformations of the technical features and principles of the present invention belong to the claimed scope of the present invention.

What is claimed is:

1. A minimally invasive bone screw fixation device for lumbar, at least comprising:
   a positioning casing comprising a rod securing base, an alignment portion and an annular notch; wherein:
   the annular notch on the positioning casing is formed between the rod securing base and the alignment portion, the rod securing base and the alignment portion are monolithically formed together; a bottom of the rod securing base has a spherical pit and a through hole arranged on a bottom center portion of the spherical pit, a top of the alignment portion has a top opening from which a screw body can enter and a passage formed from the top opening of the alignment portion to the through hole of the rod securing base to allow the screw body to move therethrough; a wall of the rod securing base has a pair of U-shaped openings aligned with each other such that a securing-base-passing passage laterally passing through the rod securing base is defined by the U-shaped openings; a wall of the alignment portion has at least two pairs of rod alignment openings and a pair of ∩-shaped openings aligned with each other, and an alignment-portion-passing passage which allows an alignment fixture to laterally pass through the alignment portion is defined by the at least two pairs of the rod alignment openings; two longitudinal notches extend respectively on the wall of the alignment portion adjacent to the rod alignment openings;
   a screw body comprising a positioning portion having a spherical head, and a screw rod; an outer diameter of the spherical head is larger than an outer diameter of the screw rod, and the spherical head connects to a top portion of the screw rod; wherein the spherical head is configured with a joint notch which conforms to a driving tool and a non-slip texture for increasing frictional force between the joint notch and the driving tool; wherein the screw rod has an outer thread, and a front portion of the screw rod is formed as a tip with an acute angle; and the screw body is rotatably connected to the bottom portion of the positioning casing and the spherical head of the screw body is located in the spherical pit of the rod securing base; the alignment portion of the positioning casing is separatably breakable from the rod securing base by applying a force to the wall of the alignment portion to irreversibly break the longitudinal notches as well as the annular notch such that the alignment portion is separated from the rod securing base.

2. The of minimally invasive bone screw fixation device for lumbar according to claim 1, wherein the pair of ∩-shaped openings are adjacent to the pair of U-shaped openings and each ∩-shaped opening communicates with each U-shaped opening, respectively.

3. The of minimally invasive bone screw fixation device for lumbar according to claim 2, wherein the shapes of the rod alignment openings are in a bulb-shaped or keyhole-shaped form with an upper portion larger than a lower portion.

4. The of minimally invasive bone screw fixation device for lumbar according to claim 1, wherein an inner surface right above the spherical pit is configured with a thread.

5. The of minimally invasive bone screw fixation device for lumbar according to claim 1, wherein the positioning casing is an elongated cup-shape hollow member with a length ranging from 85 mm to 110 mm, so that the at least two pairs of the rod alignment openings of the alignment portion remain above the skin when the bone screw is implanted into a vertebra of a human body.

6. A bone screw positioning casing for use with a screw body having a positioning portion, comprising:

a rod securing base, an alignment portion and an annular notch; wherein:

the annular notch on the positioning casing is formed between the rod securing base and the alignment portion, wherein the rod securing base and the alignment portion are monolithically formed; wherein a bottom of the rod securing base has a spherical pit and a through hole arranged on a bottom center portion of the spherical pit, a top of the alignment portion has a top opening from which a screw body can enter and a passage formed from the top opening of the alignment portion to the through hole of the rod securing base to allow the screw body to move therethrough; wherein a wall of the rod securing base has a pair of U-shaped openings aligned with each other such that a securing-base-passing passage laterally passing through the rod securing base is defined by the U-shaped openings; wherein a wall of the alignment portion has at least two pairs of rod alignment openings and a pair of ∩-shaped openings aligned with each other, and an alignment-portion-passing passages which allows an alignment fixture to laterally pass though the alignment portion is defined by the at least two pairs of rod alignment openings; two longitudinal notches extending respectively on the wall of the alignment portion adjacent to the rod alignment openings; and the positioning portion of the screw body is a spherical head and the screw body has a screw rod, the spherical pit is formed to receive the spherical head such that the positioning portion of the screw body is arranged in the spherical pit of the rod securing base and the screw body is rotatably connected to the bottom portion of the positioning casing, and the alignment portion of the positioning casing is separatably breakable from the rod securing base by applying a force to the wall of the alignment portion to irreversibly break the longitudinal notches as well as the annular notch such that the alignment portion is separated from the rod securing base.

7. The bone screw positioning casing according to claim 6, wherein of the rod alignment openings are shaped in a bulb-shaped or keyhole-shaped form with an upper portion larger than a lower portion.

8. The bone screw positioning casing according to claim 6, wherein the pair of ∩-shaped openings respectively communicate with the U-shaped openings of the rod securing base.

9. The bone screw positioning casing according to claim 6, wherein the positioning casing is an elongated cup-shape hollow member with a length ranging from 85 mm to 110 mm.

10. The bone screw positioning casing according to claim 6, wherein an inner surface right above the spherical pit is configured with a thread.

11. The bone screw positioning casing according to claim 6, wherein an outer diameter of the spherical head is larger than an outer diameter of the screw rod, the spherical head is connected to a top portion of the screw rod, the spherical head is configured with a joint notch which conforms to a driving tool and a non-slip texture for increasing frictional force between the joint notch and the driving tool; the screw rod is configured with an outer thread, and a front portion of the screw rod is formed as a tip with an acute angle; the screw body is rotatably connected to the bottom portion of the positioning casing such that the spherical head of the screw body is arranged in the spherical pit of the rod securing base.

* * * * *